US005851492A

United States Patent [19]
Blattner

[11] Patent Number: 5,851,492

[45] Date of Patent: Dec. 22, 1998

[54] MICROTITER PLATE SEALING SYSTEM

[76] Inventor: Frederick R. Blattner, 1547 Jefferson St., Madison, Wis. 53711

[21] Appl. No.: 940,824

[22] Filed: Sep. 30, 1997

[51] Int. Cl.[6] ........ C12M 1/38

[52] U.S. Cl. ........ 422/102; 422/109; 435/305.3; 435/288.4; 220/523; 220/526; 220/232

[58] Field of Search ........ 422/102, 104, 422/109; 435/288.4, 305.3; 220/232, 523, 526

[56] References Cited

U.S. PATENT DOCUMENTS

| | | | |
|---|---|---|---|
| 2,771,399 | 11/1956 | Savage . | |
| 4,096,965 | 6/1978 | Lessnig et al. | 220/232 |
| 4,772,453 | 9/1988 | Lisenbee | 422/52 |
| 4,814,279 | 3/1989 | Sugaya . | |
| 5,186,899 | 2/1993 | Drago et al. . | |
| 5,273,718 | 12/1993 | Sköld et al. . | |
| 5,604,130 | 2/1997 | Warner et al. | 435/286.7 |

*Primary Examiner*—Jeffrey Snay
*Attorney, Agent, or Firm*—Quarles & Brady

[57] ABSTRACT

An apparatus for sealing and maintaining a desired temperature of a sample holder includes a non-deformable support, a deformable diaphragm secured to the lower surface of the support and a thermal regulable heater in thermal connection with the diaphragm. The apparatus can be positioned above the upper surface of a sample holder and, upon inflation of the diaphragm, a seal is formed between the diaphragm and the sample holder. When the thermoregulable heating element is activated, the sample holder is maintained at the desired temperature. The temperature can be coordinately regulated with a block heater that heats the underside of the sample holder.

13 Claims, 2 Drawing Sheets

MICROTITER PLATE SEALING SYSTEM

BACKGROUND OF THE INVENTION

The present invention relates to the field of analytic instrumentation, and more specifically to the field of treatment of samples in microtiter plates in molecular biological methods. Many molecular biological reactions are performed in very small volumes, typically on the order of 100 μl or less. Many such reactions are repetitive analyses of multiple samples. Such small volume reactions are often performed in sample holders adapted to hold multiple samples. Most typically, such sample holders are microtiter dishes that include 96 individual wells in which separate small volume reactions can be processed. Microtiter dishes having fewer or more sample wells are also available.

In a typical set of reactions, copies of a DNA or protein molecule are aliquoted into a separate sample wells and are processed under various conditions or in the presence of various reactants. The Polymerase Chain Reactions and DNA sequence analysis reactions are both conveniently performed in microtiter wells.

One shortcoming recognized in the art that seeks to process such repetitive reactions in microtiter sample holders is the inability to maintain both a tight seal on the sample wells and a constant temperature throughout the wells. When the typically small volumes of these reactions are heated, sample evaporation is a common and undesirable result. The response to the evaporation problems has been to trap each small sample beneath an amount of mineral oil. However, the amount of mineral oil needed is often more than the total sample volume and it is difficult to retrieve the mineral oil without retrieving some of the sample as well. Another response to the problem has been to seal the sample wells, although this often leads to sample condensation on the sealant. However, because the reactions are performed in such small volumes, even a small sample loss can eliminate the chance of obtaining valuable data. Moreover, it is difficult to reproducibly return condensed material into its sample well.

Finally, microtiter dishes, which are generally disposable and formed of plastic, tend to warp when heated making complete contact between the dish and the heater difficult. This can lead to inconsistent heating and irreproducible results.

BRIEF SUMMARY OF THE INVENTION

The present invention is summarized in that an apparatus for maintaining a seal on a sample holder includes a support having a lower surface, a deformable diaphragm attached to the lower surface of the support, and a thermoregulable heater in thermal connection with the diaphragm. The diaphragm and the support define a chamber that can be inflated as desired. When the chamber is inflated, the diaphragm engages the sample holder to form a gas-tight seal between the chamber and at least one well of the sample holder.

It is an object of the present invention to provide an apparatus that seals a well in a sample holder and permits the temperature at such a seal to be regulated in a desired manner.

It is another object of the present invention that the sealing apparatus can be coordinately thermoregulated with an optional thermoregulated heater block beneath the samples.

It is yet another object of the present invention to provide a thermoregulable seal that exerts pressure onto the sample holder to maximize contact between the sample holder and an optional heater block.

It is a feature of the present invention that the diaphragm that engages the upper surface of the sample holder is deformable, allowing the gas container to form a complete gas-tight seal within the wells.

It is an advantage of the present invention that the diaphragm can be maintained at a desired temperature because the heating elements are attached to or embedded within the diaphragm itself.

Other objects, advantages, and features will become apparent upon consideration of the following detailed description of the preferred embodiments, considered in conjunction with the accompanying drawings.

BRIEF DESCRIPTION OF THE SEVERAL VIEWS OF THE DRAWINGS

FIG. 3 shows the apparatus with uninflated chamber, while FIG. 4 shows the chamber inflated and the diaphragm in contact with a microtiter plate.

DETAILED DESCRIPTION OF THE INVENTION

FIGS. 1–4 show a preferred embodiment of an apparatus 10 designed in accordance with the present invention, for sealing and thermoregulating the wells of a sample holder. The sealing function can be employed without thermal regulation, which may be particularly useful for reactions that do not require heating to high temperature (e.g., 68° C. or higher).

Figure 1:
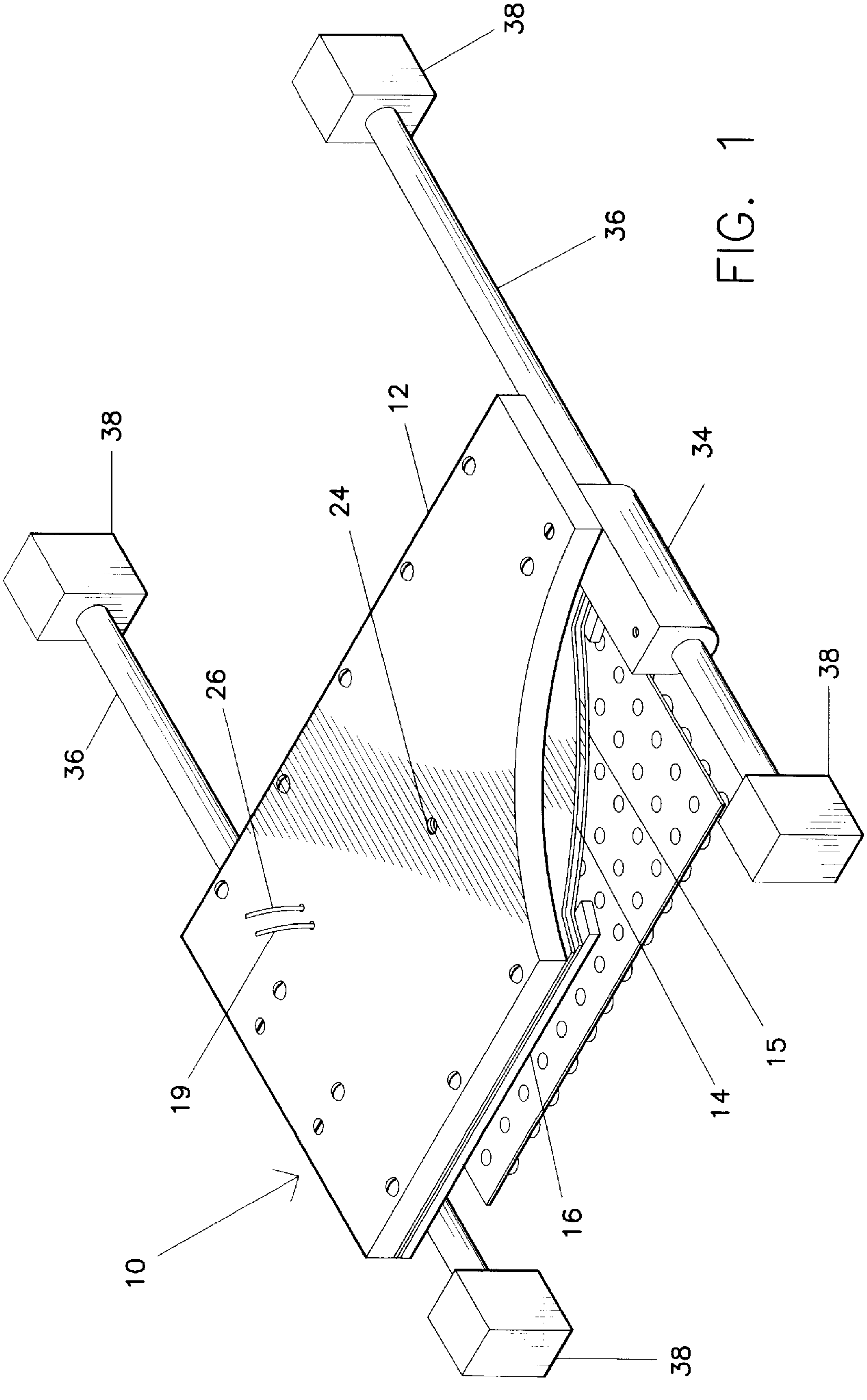
FIG. 1 shows a preferred embodiment of the apparatus of the present invention shown in conjunction with a microtiter dish for receiving samples.
Figure 2:
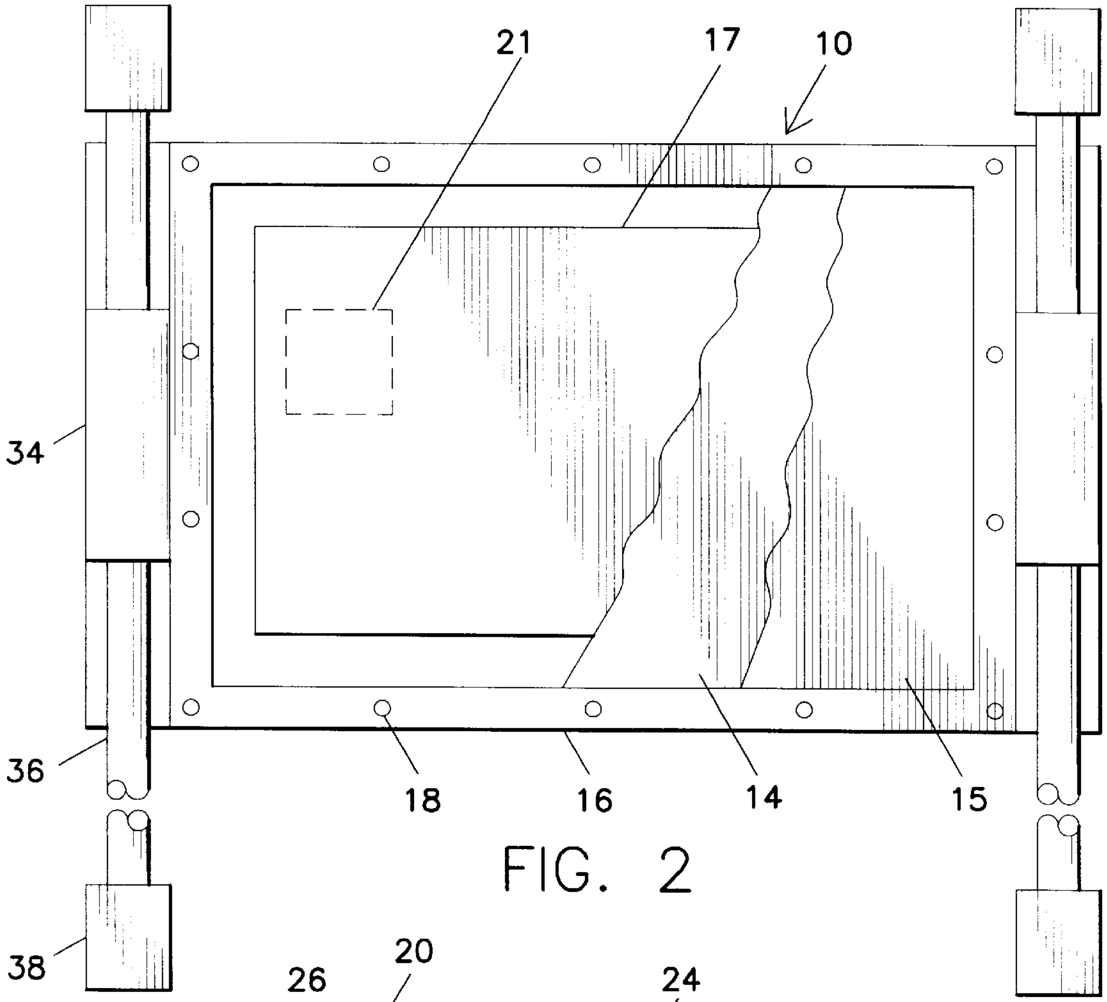
FIG. 2 shows a cutaway view of the underside of the preferred embodiment of FIG. 1.
Figure 3:
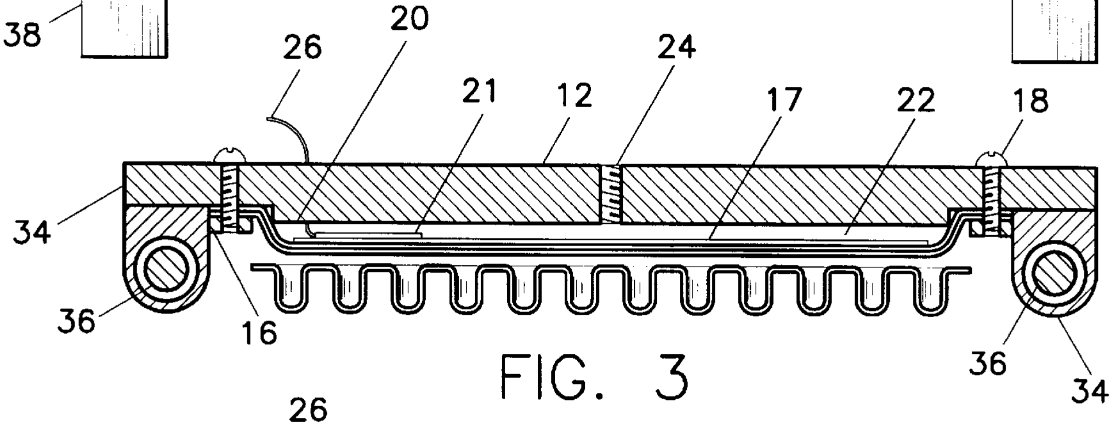
FIGS. 3 and 4 show a preferred embodiment of the present invention in use.

Referring first to FIG. 1, the preferred embodiment 10 includes a rectangular support 12 in the approximate size and shape of a microtiter dish. The use of the invention is not limited to sealing microtiter wells; rather, sample holders having other sizes and shapes can also be sealed and/or heated according to the same principles. The support 12 is formed of a rigid material, such as aluminum or a plastic, that retains its shape at temperatures up to about 100° C. It is also desired that the material be relatively light and inexpensive. Secured to the lower surface of the support 12 is an inflatable, deformable membranous diaphragm 14 that can be formed of any strong, flexible material that retains its strength, integrity, flexibility and inflatability at temperatures up to about 100° C. A silicon rubber diaphragm having a sheet thickness of 0.033 inches is suitable. A cover sheet 15 can be provided to keep the diaphragm separate from the samples. The cover sheet 15 should not interfere with thermal contact between the diaphragm and the samples and can be a thin plastic sheet, such as an acetate sheet. The diaphragm 14 and the cover sheet 15 are secured at their perimeter to the lower surface of the support 12 with a rectangular bezel 16 sized and shaped to conform to the dimensions of the support 12. The bezel 16 is itself held in place by screws 18 that pass through the bezel 16 and the support 12. The bezel 16, like the support 12, should be non-deformable at temperatures up to about 100° C. so that it restrains the diaphragm 14 securely in place. Aluminum is a suitable material for forming the bezel 16. A portion 20 of the support 12 within the perimeter of bezel 16 can be thicker than the perimeter of the support 12, to provide additional thermal insulation to reduce loss of thermal energy from the diaphragm 14 through the support 12.

The lower surface of the support 12 and the secured diaphragm 14 define therebetween an inflatable chamber 22 for receiving a gas. A gas inlet 24, in fluid communication with the inflatable chamber, facilitates gas flow into and out of the inflatable chamber 22. In the embodiment exemplified in FIGS. 1–4, the gas inlet 24 is a conduit from the inflatable chamber 22 that passes through the support 12 to the exterior of the apparatus 10. At the exterior, the gas inlet 24 is adapted for attachment to a flow-controllable source of gas, such as compressed air for inflating the inflatable chamber, or to a vacuum pump for rapidly deflating the inflatable chamber. The inflation/deflation functions can be performed manually by an operator or can be automated, in a manner known to the art, by providing a mechanical or electronic controller. The gas controlling function can be provided on the gas inlet 24 itself, by providing valving means in fluid communication with the conduit.

The apparatus also includes a thermoregulable heating element in thermal connection with the diaphragm 14. "In thermal connection" means that heat generated by the heating element transfers to the diaphragm 14 itself, thereby maintaining the diaphragm at a desired temperature. In the exemplified embodiment, the thermoregulable heating element includes a flexible, conductive ribbon 17 secured by thermoresistant adhesive to the surface of the diaphragm 14 that forms the interior of the inflatable chamber. The ribbon 17 or like temperature-controlling element could also be embedded within the diaphragm itself. It is preferred that the element be sufficiently flexible to conform to the shape of the diaphragm when chamber 22 is inflated. The element could also be based on other heating forms, such as heated water passing through open channels, although such a system would be less preferred since the ability to regulate the temperature rapidly could be impaired and since production of a diaphragm having open channels might be more difficult.

The ribbon 17 is attached to leads 19 that pass through the support 12 and are connectable by an electrical circuit to a thermoregulator or an electric heater (not shown). A suitable thermoregulator would be a variable-voltage transformer that can be manually or automatically controlled.

A temperature sensor, such as a thermocouple 21, is also provided in thermal contact with the ribbon 17 for monitoring the temperature of the ribbon 17 via leads 26 that can connect to a temperature monitor. The monitor can direct the thermoregulator to adjust the temperature of the heating element, as needed. The thermocouple 21 can be attached to the ribbon 17 using a thermoresistant adhesive.

The leads 19 and 26 associated with monitoring and adjusting the temperature of the conductive ribbon must not interfere with the ability of the diaphragm 14 to form a seal with the wells formed into the upper surface of the sample holder, and thus it is preferred that the leads 19 and 26 pass out of the apparatus through the top of the support as shown in FIG. 1.

For convenience, the entire assembly thus described can be provided with bearing holders 34 affixed to the support 12 and slidably mounted on parallel rails 36. As shown, the rails 36 can be provided with mounts 38 for securing the apparatus 10 to other sample processing hardware. Although two bearing holders 34 and two rails 36 are shown, the same effect can be accomplished using a single rail on one side of the apparatus and a countersupport on the other side, for retaining the apparatus 10 in a generally horizontal position. Alternatively, the apparatus 10 could be movably positioned over or away from a sample holder by providing a hinge along one edge or by allowing the apparatus to pivot in a horizontal plane about a vertical axis. Any of these solutions would achieve the desired results of exposing the sample holder during sample loading and covering the sample holder during sample processing.

In use, the apparatus will typically be secured to a base that supports the sample holder, although the precise nature of the base will vary with the intended use of the apparatus. The temperature of the base can be controlled, for example, by flowing water through the base or by providing an electrical circuit of the sort described in connection with the invention. By providing a suitable controller, the invention and the base can be coordinately controlled. Movement of the apparatus 10 above the base can be controlled electrically or electro-mechanically. A preferred sample processing hardware would be a thermal heating block or a thermal cycler of the sort used in connection with polymerase chain reactions or other reactions performed at temperatures other than ambient temperature.

The operating principle of the invention is as follows. A sample holder, preferably a microtiter dish, is readied for processing with samples and/or reagents. The sample holder is secured in a base and the apparatus of the present invention is then positioned above the sample holder so that the gas container secured to the support is above the wells of the sample holder, as in FIGS. 1, 3, and 4. In the preferred embodiments, the positioning is accomplished by sliding the apparatus 10 along the rails until it is positioned as desired. When the apparatus is positioned above the sample, suitable clearance should be allowed between the two so as to prevent jarring contact. A suitable clearance between the samples and the uninflated diaphragm is less than about 0.25 inches and is most preferably about 0.05 inches.

Figure 4:
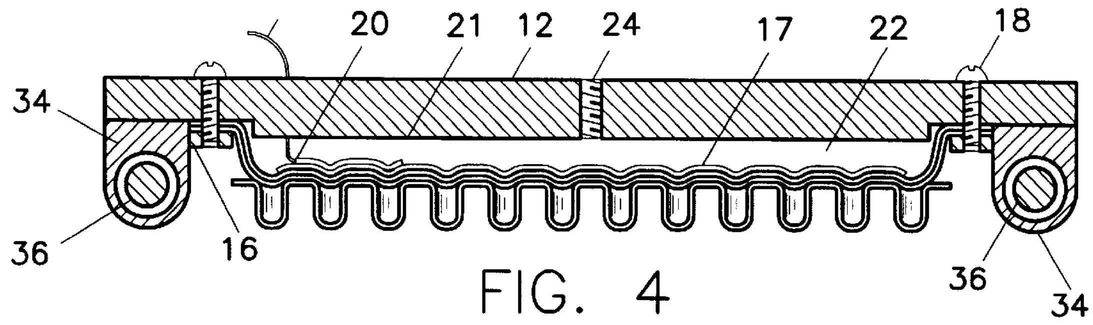

The gas, preferably air, is admitted into the inflatable chamber through the inlet valve 24 until a gas-tight seal is made between the lower surface of the diaphragm and the wells formed in the upper surface of the microtiter dish (FIG. 4). When this level of inflation has been reached, gas pressure inside the inflatable chamber can be maintained to keep the diaphragm in an inflated state.

Once the wells have been sealed by the gas container, any necessary heating or thermocycling may begin. While it is possible to heat the sample holder only from above or below, it is generally preferred that the samples be heated both from below and from above if significant temperature increases or temperature variations between the tops and bottoms of the sample wells are anticipated. To avoid condensation problems, it is most preferred that the temperature at the bottoms and tops of the microtiter wells be the same, to avoid having a cooler surface on which the sample can condense. Accordingly, it is preferred that a thermal block heater be provided beneath the sample holder, and the heating element of the present invention, be coordinately regulated, preferably by a controllable thermoregulator that can vary the temperature at both sites according to a predefined profile by, for instance, varying the voltage supplied to both the upper heating element and the lower thermal block heater. Devices that regulate the temperature profile of heating blocks are well known and it is well within the skill level in the art to connect the heating element of the present invention to such a thermoregulator. If such thermal control is desired, then it is most advantageous to also provide thermal sensors on the gas container and the heating block that can provide feedback control to the thermal regulator.

When the desired reaction temperature profile has been completed, the gas pressure is released from the inflatable chamber. It is preferred that this pressure release be performed at a controlled, constant rate using a vacuum pump, so as to avoid any disruption to the samples. It is also desirable that the gas removed from the inflatable chamber be vented away from the samples, again so as not to disrupt the samples.

In addition to providing the sample cover and heating functions, the inflatable gas container also applies pressure to the microtiter dish itself, thereby maximizing contact between the dish and the lower thermal block, and likewise maximizing the thermal connection between the two. By providing a thermally-regulable seal, the invention eliminates the need for mineral oil and avoids the problems of sample condensation that have plagued the art.

Although the present invention is described in terms of the preferred embodiments exemplified herein, it is to be understood that the invention is not to be so limited. In particular, one of ordinary skill can readily envision modifications to the apparatus in the positioning, heating, and inflation aspects of the disclosed embodiments. Although the apparatus is exemplified as providing a heating seal for one sample holder, it is also envisioned that this invention can be applied to systems accommodating more than one sample holder. It is specifically envisioned that the present invention can be incorporated, as part of an apparatus for robotic or automated sample processing such as, without limitation, an apparatus for performing automated DNA sequencing reactions or blood/urine analysis. The invention is intended to cover all such modifications and variations as come within the scope of the following claims.

I claim:

1. An apparatus for sealing and maintaining a desired temperature within at least one well formed into an upper surface of a sample holder, the apparatus comprising:

a support having a lower surface;

a deformable diaphragm secured to the lower surface of the support so that the support and the diaphragm define an inflatable chamber therebetween; and a thermoregulable heating element in thermal connection with the diaphragm, wherein when the diaphragm is interposed between the support and the upper surface of the sample holder and the chamber is inflated, a surface of the diaphragm engages the sample holder to form a gas-tight seal between the diaphragm and the at least one well thereby maintaining a desired temperature at the seal.

2. An apparatus as claimed in claim 1 further comprising a gas inlet in fluid communication with the inflatable chamber.

3. An apparatus as claimed in claim 1 wherein the diaphragm is a silicone rubber sheet.

4. An apparatus as claimed in claim 1 further comprising at least one rail and at least one bearing holder, the bearing being affixed to the support and slidably mounted on the at least one rail for positioning the support above the upper surface of the sample holder.

5. An apparatus as claimed in claim 1 wherein the thermoregulable heating element is attached to a surface of the diaphragm that does not engage the sample holder.

6. An apparatus as claimed in claim 1 wherein the thermoregulable heating element is embedded in the diaphragm.

7. An apparatus as claimed in claim 1 further comprising a controllable thermoregulator in electrical communication with the thermoregulable heating element.

8. An apparatus as claimed in claim 7 further comprising a thermoregulable thermal block heater, wherein both the thermoregulable thermal block heater and the thermoregulable heating element are in electrical communication with the controllable thermoregulator.

9. An apparatus for sealing and maintaining a desired temperature within at least one well formed into an upper surface of a sample holder, the apparatus comprising:

a support having a lower surface;

a deformable diaphragm secured to the lower surface of the support, the secured diaphragm and the lower surface of the support defining therebetween an inflatable chamber;

a gas inlet in fluid communication with the inflatable chamber;

a thermoregulable thermal heating element in thermal connection with the diaphragm; and a thermoregulable thermal block heater under coordinated thermal control with the heating element, wherein when the diaphragm is interposed between the support and the upper surface of the microtiter dish, and when a gas inflates the inflatable chamber, a surface of the diaphragm engages the sample holder to form a gas-tight seal between the diaphragm and the at least one well thereby maintaining a desired temperature at the seal.

10. An apparatus as claimed in claim 9 wherein the diaphragm is a silicone rubber sheet.

11. An apparatus as claimed in claim 9 further comprising at least one rail and at least one bearing holder affixed to the support and slidably mounted on the at least one rail for positioning the support above the upper surface of the microtiter dish.

12. An apparatus as claimed in claim 9 further comprising a controllable thermoregulator in electrical communication with the thermoregulable heating element.

13. An apparatus as claimed in claim 12, wherein both the thermoregulable thermal block heater and the thermoregulable heating element are in electrical communication with the controllable thermoregulator.

* * * * *